US00PP19284P2

(12) United States Plant Patent
Hofmann

(10) Patent No.: US PP19,284 P2
(45) Date of Patent: Oct. 7, 2008

(54) ***BEGONIA* PLANT NAMED 'INNBELLWHI'**

(50) Latin Name: *Begonia×tuberhybrida*
Varietal Denomination: Innbellwhi

(75) Inventor: Silvia Hofmann, Mainz (DE)

(73) Assignee: Innovaplant GmbH & Co. KG, Gensingen (DE)

( * ) Notice: Subject to any disclaimer, the term of this patent is extended or adjusted under 35 U.S.C. 154(b) by 0 days.

(21) Appl. No.: 11/888,427

(22) Filed: Aug. 1, 2007

(51) Int. Cl.
*A01H 5/00* (2006.01)

(52) U.S. Cl. ..... Plt./345
(58) Field of Classification Search ..... Plt./345
See application file for complete search history.

*Primary Examiner*—Kent L Bell
(74) *Attorney, Agent, or Firm*—C. A. Whealy

(57) ABSTRACT

A new and distinct cultivar of *Begonia* plant named 'Innbellwhi', characterized by its compact, mounded and pendulous plant habit; freely branching habit; and numerous flowers that are white in color.

1 Drawing Sheet

Botanical designation: *Begonia×tuberhybrida.*
Cultivar denomination: 'Innbellwhi'.

BACKGROUND OF THE INVENTION

The present invention relates to a new and distinct cultivar of *Begonia* plant, botanically known as *Begonia× tuberhybrida,* commercially known as hybrid tuberose *Begonia,* and hereinafter referred to by the name 'Innbellwhi'.

The new *Begonia* is a product of a planned breeding program conducted by the Inventor in Gensingen, Germany. The objective of the breeding program was to develop new hybrid tuberose *Begonia* cultivars with attractive flower form and color.

The new *Begonia* originated from a cross-pollination made by the Inventor in 2005 of a proprietary selection of *Begonia×tuberhybrida* identified as code number BO4 3-56, not patented, as the female, or seed, parent with a proprietary selection of *Begonia×tuberhybrida* identified as code number BO4 3-91, not patented, as the male, or pollen, parent. The new *Begonia* was discovered and selected by the Inventor from within the progeny of the stated cross-pollination in a controlled environment in Gensingen in 2005.

Asexual reproduction of the new *Begonia* by cuttings in a controlled environment in Gensingen, Germany since the summer of 2005, has shown that the unique features of this new *Begonia* are stable and reproduced true to type in successive generations.

SUMMARY OF THE INVENTION

The cultivar Innbellwhi has not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Innbellwhi'. These characteristics in combination distinguish 'Innbellwhi' as a new and distinct cultivar of *Begonia:*

1. Compact, mounded and pendulous plant habit.
2. Freely branching habit.
3. Numerous flowers that are white in color.

Plants of the new *Begonia* differ from plants of the female parent selection in the following characteristics:

1. Plants of the new *Begonia* are more compact than plants of the female parent selection.
2. Plants of the new *Begonia* and the female parent selection differ in flower color as plants of the female parent selection have pink-colored flowers.

Plants of the new *Begonia* differ from plants of the male parent selection in the following characteristics:

1. Plants of the new *Begonia* are more upright than plants of the male parent selection.
2. Plants of the new *Begonia* and the male parent selection differ in flower color as plants of the male parent selection have soft pink-colored flowers.

Plants of the new *Begonia* can also be compared to plants of the cultivar Elserta, not patented. In side-by-side comparisons conducted in Gensingen, Germany, plants of the new *Begonia* differed from plants of the cultivar Elserta in the following characteristics:

1. Plants of the new *Begonia* were more compact than plants of the cultivar Elserta.
2. Plants of the new *Begonia* and the cultivar Elserta differed in flower color as plants of the cultivar Elserta had orange red-colored flowers.

BRIEF DESCRIPTION OF THE PHOTOGRAPHS

The accompanying colored photographs illustrate the overall appearance of the new *Begonia,* showing the colors as true as it is reasonably possible to obtain in colored reproductions of this type. Colors in the photographs may differ slightly from the color values cited in the detailed botanical description which accurately describe the colors of the new *Begonia.*

The photograph at the bottom of the sheet comprises a side perspective view of a typical flowering plant of 'Innbellwhi' grown in a container.

The photograph at the top of the sheet is a close-up view of typical flowers and flower buds of 'Innbellwhi'.

DETAILED BOTANICAL DESCRIPTIONS

In the following description, color references are made to The Royal Horticultural Society Colour Chart, 1995 Edition, except where general terms of ordinary dictionary significance are used. Plants used for the aforementioned photograph and following observations and measurements were grown in Bonsall, Calif. in 15-cm containers and under commercial practice in a polycarbonate-covered greenhouse during the spring and summer. During the production of the plants, day temperatures averaged 21° C., night temperatures averaged 18° C. and light levels were about 5,000 foot-candles. Plants used for the photographs and the description were about one month from planting.

Botanical classification: *Begonia×tuberhybrida* cultivar Innbellwhi.

Parentage:

*Female, or seed, parent.*—Proprietary selection of *Begonia×tuberhybrida* identified as code number BO4 3-56, not patented.

*Male, or pollen, parent.*—Proprietary selection of *Begonia×tuberhybrida* identified as code number BO4 3-91, not patented.

Propagation:

*Type.*—By terminal vegetative cuttings.

*Time to initiate roots, summer.*—About 15 days at temperatures of about 18° C.

*Time to initiate roots, winter.*—About 25 days at temperatures of about 18° C.

*Time to produce a rooted young plant, summer.*—About 25 days at temperatures of about 18° C.

*Time to produce a rooted young plant, winter.*—About 30 to 35 days at temperatures of about 18° C.

*Root description.*—Medium to thin, fibrous; ivory in color. Plants of the new *Begonia* have not been observed to form tubers.

*Rooting habit.*—Moderately branching; moderately dense.

Plant description:

*Plant form.*—Compact, mounded and pendulous plant habit; freely basal branching with about five primary branches per plant; primary branches with secondary branches at potentially every node. Moderately vigorous growth habit.

*Plant height.*—About 13.5 cm.

*Plant width.*—About 23 cm.

*Branch description.*—Length: About 11.5 cm. Diameter: About 7 mm. Internode length: About 1.3 cm. Texture: Smooth, glabrous. Color: 146C.

*Leaf description.*—Arrangement: Alternate, simple. Length: About 10.3 cm. Width: About 4 cm. Shape: Lanceolate with reniform tendencies. Apex: Acuminate. Base: Obliquely cordate. Margin: Serrate. Texture, upper and lower surfaces: Smooth, glabrous. Venation pattern: Palmate to pinnate. Color: Developing leaves, upper surface: 138A. Developing leaves, lower surface: 147C. Fully expanded leaves, upper surface: 137A; venation, 145A. Fully expanded leaves, lower surface: 147C; venation, 148C. Petiole length: About 2.7 cm. Petiole diameter: About 2.5 mm. Petiole texture, upper and lower surfaces: Smooth, glabrous; occasionally with scattered hairs. Petiole color, upper and lower surfaces: 194A.

Flower description:

*Flowering habit.*—Sterile double flowers with numerous tepals; flowers auxillary and typically arranged in pendulous clusters of two. Freely flowering habit with about eight flowers and flower buds per branch. Flowers not fragrant.

*Natural flowering season.*—Plants flower continuously during the spring in Germany. Flowers last about four to five days on the plant. Flowers not persistent.

*Flowers.*—Shape: Rounded to ovate. Diameter: About 5.4 cm. Depth (height): About 3 cm.

*Flower buds.*—Shape: Ovoid. Length: About 2.7 cm. Diameter: About 2.2 cm. Color: Close to 145D.

*Tepals.*—Arrangement: Rosette. Quantity per flower: About 78 in numerous whorls. Length: About 2.6 cm. Width: About 1 cm. Shape: Elliptical. Apex: Acute. Base: Attenuate. Margin: Entire. Texture, upper and lower surfaces: Smooth, glabrous. Color: When opening, upper and lower surfaces: 155D. Fully opened, upper and lower surfaces: 155D.

*Flower bracts.*—Quantity/arrangement: Two, opposite. Length: About 2.7 cm. Diameter: About 2.4 cm. Shape: Elliptical. Apex: Acute. Base: Truncate. Margin: Entire. Texture, upper and lower surfaces: Smooth, glabrous. Color, upper surface: 157C. Color, lower surface: 157D.

*Peduncles.*—Angle: Drooping. Length: About 2.7 cm. Diameter: About 2 mm. Texture: Smooth, glabrous. Color: 145C.

*Reproductive organs.*—Stamens: None observed. Pistils: None observed. Seed/fruit: Seed and fruit production have not been observed.

Disease/pest resistance: Resistance to pathogens and pests common to *Begonia* has not been observed.

Temperature tolerance: Plants of the new *Begonia* have been observed to tolerate temperatures from about 16° C. to about 35° C.

It is claimed:

1. A new and distinct *Begonia* plant named 'Innbellwhi' as illustrated and described.

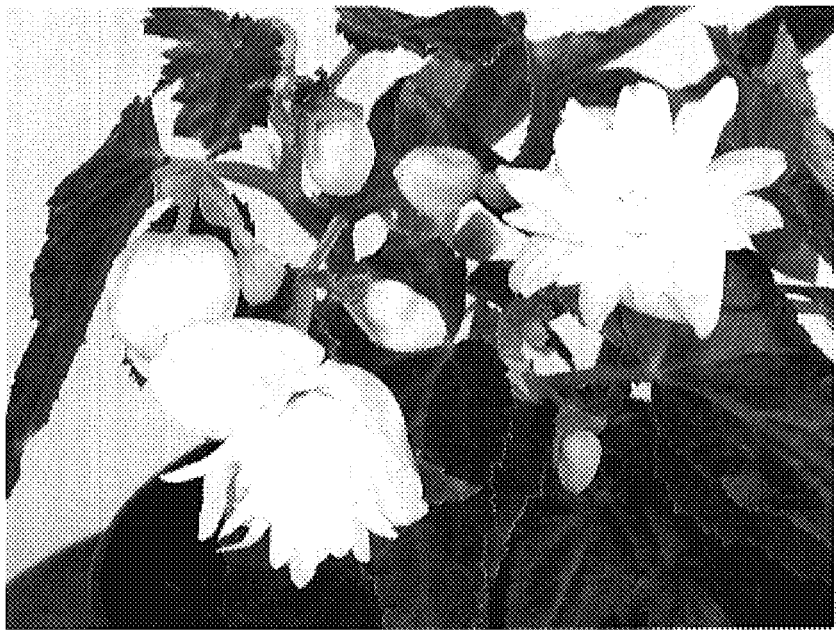
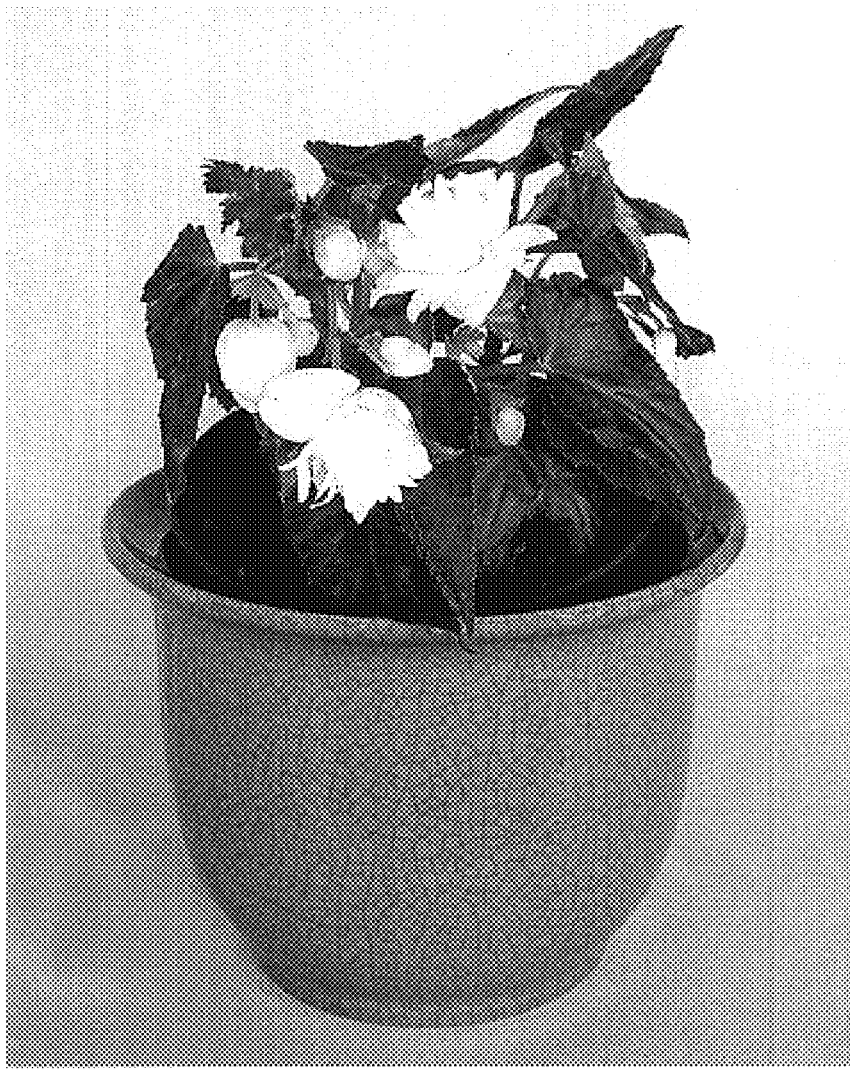

* * * * *